(12) United States Patent
Schurman et al.

(10) Patent No.: US 7,510,849 B2
(45) Date of Patent: Mar. 31, 2009

(54) OCT BASED METHOD FOR DIAGNOSIS AND THERAPY

(75) Inventors: Matthew J. Schurman, Somerset, NJ (US); Walter Jeffrey Shakespeare, Macungie, PA (US)

(73) Assignee: GlucoLight Corporation, Bethlehem, PA (US)

( * ) Notice: Subject to any disclaimer, the term of this patent is extended or adjusted under 35 U.S.C. 154(b) by 0 days.

(21) Appl. No.: 11/040,388

(22) Filed: Jan. 21, 2005

(65) Prior Publication Data

US 2005/0186648 A1 Aug. 25, 2005

Related U.S. Application Data

(60) Provisional application No. 60/540,082, filed on Jan. 29, 2004.

(51) Int. Cl.
C12Q 1/54 (2006.01)
(52) U.S. Cl. .......................................... 435/14; 424/9.1
(58) Field of Classification Search ...................... None
See application file for complete search history.

(56) References Cited

U.S. PATENT DOCUMENTS

| | | |
|---|---|---|
| 3,826,905 A | 7/1974 | Valkama et al. |
| 3,958,560 A | 5/1976 | March |
| 4,014,321 A | 3/1977 | March |
| 4,476,875 A | 10/1984 | Nilsson et al. |
| 4,590,948 A | 5/1986 | Nilsson |
| 4,606,351 A | 8/1986 | Lübbers |
| 4,655,225 A | 4/1987 | Dähne et al. |
| 4,704,029 A | 11/1987 | Van Heuvelen |
| 4,731,363 A | 3/1988 | Hamilton et al. |
| 4,743,604 A | 5/1988 | Alig et al. |
| 4,750,830 A | 6/1988 | Lee |
| 4,834,111 A | 5/1989 | Khanna et al. |
| 4,871,755 A | 10/1989 | Alig et al. |
| 4,873,989 A | 10/1989 | Einzig |
| 4,882,492 A | 11/1989 | Schlager |
| 4,883,953 A | 11/1989 | Koashi et al. |
| 4,890,621 A | 1/1990 | Hakky |
| 4,901,728 A | 2/1990 | Hutchinson |
| 4,948,248 A | 8/1990 | Lehman |
| 4,979,509 A | 12/1990 | Hakky |
| 4,989,978 A | 2/1991 | Groner |
| 5,025,785 A | 6/1991 | Weiss |
| 5,028,787 A | 7/1991 | Rosenthal et al. |
| 5,054,487 A | 10/1991 | Clarke |
| 5,070,874 A | 12/1991 | Barnes et al. |
| 5,101,814 A | 4/1992 | Palti |
| 5,112,124 A | 5/1992 | Harjunmaa et al. |
| 5,115,133 A | 5/1992 | Knudson |
| 5,168,325 A | 12/1992 | Yoder-Short |
| 5,178,153 A | 1/1993 | Einzig |
| 5,209,231 A | 5/1993 | Cote et al. |
| 5,222,495 A | 6/1993 | Clarke et al. |
| 5,222,496 A | 6/1993 | Clarke et al. |
| 5,243,983 A | 9/1993 | Tarr et al. |
| 5,267,152 A | 11/1993 | Yang et al. |
| 5,277,181 A | 1/1994 | Mendelson et al. |
| 5,313,941 A | 5/1994 | Braig et al. |
| 5,321,501 A | 6/1994 | Swanson et al. |
| 5,341,805 A | 8/1994 | Stavridi et al. |
| 5,348,003 A | 9/1994 | Caro |
| 5,349,953 A | 9/1994 | McCarthy et al. |
| 5,361,758 A | 11/1994 | Hall et al. |
| 5,370,114 A | 12/1994 | Wong et al. |
| 5,376,336 A | 12/1994 | Lübbers et al. |
| 5,379,238 A | 1/1995 | Stark |
| 5,383,452 A | 1/1995 | Buchert |
| 5,398,681 A | 3/1995 | Kupershmidt |

(Continued)

FOREIGN PATENT DOCUMENTS

EP 0282234 9/1988

(Continued)

OTHER PUBLICATIONS

Larin et al, "Noninvasive Blood Glucose Monitoring With Optical Coherence Tomography," (Diabetes Care), vol. 25, 2002, pp. 2263-2267.*

(Continued)

*Primary Examiner*—Cecilia Tsang
*Assistant Examiner*—Amanda P Wood
(74) *Attorney, Agent, or Firm*—Thomas J. Engellenner; Charlton Shen; Nutter McClennen & Fish LLP

(57) ABSTRACT

This invention relates to a method of diagnosing or treating a biological subject, such as a person or animal, comprising the steps of subjecting at least a microsample of the subject's tissue to a physiological perturbation and measuring the response of the microsample to the perturbation using optical coherence tomography (OCT). In an exemplary embodiment, the concentration of glucose in the microsample is perturbed, as by providing the subject with a high glucose drink, and subsequently monitoring at a high sample rate in a microsample by OCT. Pathology, such as diabetes, can be diagnosed by deviation of the concentration vs. time response over several cells (micro-oscillation) from the micro-oscillation in the cells of a healthy subject. Other applications include diagnosing or treating de-hydration and diseases that cause changes in the osmolyte concentrations and thus the osmotic pressure in the cells in tissue.

13 Claims, 3 Drawing Sheets

U.S. PATENT DOCUMENTS

| | | | |
|---|---|---|---|
| 5,433,197 | A | 7/1995 | Stark |
| 5,435,309 | A | 7/1995 | Thomas et al. |
| 5,448,992 | A | 9/1995 | Kupershmidt |
| 5,452,716 | A | 9/1995 | Clift |
| 5,457,535 | A | 10/1995 | Schmidtke et al. |
| 5,459,570 | A | 10/1995 | Swanson et al. |
| 5,492,118 | A | 2/1996 | Gratton et al. |
| 5,501,226 | A | 3/1996 | Petersen et al. |
| 5,535,743 | A | 7/1996 | Backhaus et al. |
| 5,549,114 | A | 8/1996 | Petersen et al. |
| 5,551,422 | A | 9/1996 | Simonsen et al. |
| 5,553,616 | A | 9/1996 | Ham et al. |
| 5,582,168 | A | 12/1996 | Samuels et al. |
| 5,710,630 | A | 1/1998 | Essenpreis et al. |
| 5,795,295 | A | 8/1998 | Hellmuth et al. |
| 6,036,919 | A | 3/2000 | Thym et al. |
| 6,147,108 | A | 11/2000 | Hauptman |
| 6,294,062 | B1 | 9/2001 | Buck, Jr. et al. |
| 6,425,863 | B1 | 7/2002 | Werner et al. |
| 6,443,881 | B1 | 9/2002 | Finger |
| 6,541,216 | B1 | 4/2003 | Wilsey et al. |
| 6,544,212 | B2 | 4/2003 | Galley et al. |
| 6,556,853 | B1 | 4/2003 | Cabib et al. |
| 6,572,566 | B2 | 6/2003 | Effenhauser |
| 6,707,554 | B1 | 3/2004 | Miltner et al. |
| 6,725,073 | B1 | 4/2004 | Motamedi et al. |
| 6,780,651 | B2 | 8/2004 | Douglas et al. |
| 6,837,337 | B2 | 1/2005 | Thomas et al. |
| 6,990,364 | B2 | 1/2006 | Ruchti et al. |
| 2002/0016533 | A1 | 2/2002 | Marchitto et al. |

FOREIGN PATENT DOCUMENTS

| | | |
|---|---|---|
| EP | 0160768 | 5/1989 |
| EP | 0127947 | 8/1990 |
| EP | 0280986 | 7/1992 |
| EP | 0317121 | 2/1994 |
| EP | 0536187 | 9/1994 |
| EP | 0589191 | 3/1997 |
| EP | 0603658 | 2/1999 |
| EP | 0631137 | 3/2002 |
| EP | 0670143 | 5/2003 |
| WO | WO 88/06726 | 9/1988 |
| WO | WO 89/10087 | 11/1989 |
| WO | WO 91/18548 | 12/1991 |
| WO | WO 92/10131 | 6/1992 |
| WO | WO 92/17765 | 10/1992 |
| WO | WO 93/00855 | 1/1993 |
| WO | WO 93/07801 | 4/1993 |
| WO | WO 93/09421 | 5/1993 |
| WO | WO 93/16629 | 9/1993 |
| WO | WO 94/04070 | 3/1994 |
| WO | WO 94/13193 | 6/1994 |
| WO | WO 95/32416 | 11/1995 |

OTHER PUBLICATIONS

Arnold, M.A., et al, "Determination of Physiological Levels of Glucose in an Aqueous Matrix with Digitally Filtered Fourier Transform Near-infrared Spectra," Anal. Chem., vol. 64, No. 14, pp. 1457-1464 (1990).

Arnold, V.W., "Fourier transformation infrared spectrometry—a new (old) method of detection in forensic chemistry and criminal investigation," Beitr Gerichtl Med., vol. 47, pp. 123-147 (1989).

Bruuisema, J. T., "Correlation between blood glucose concentration in diabetics and noninvasively measured tissue optical scattering coefficient," Opt. Lett., vol. 22, No. 3, pp. 190-193 (1997).

Burritt, M.F., "Current analytical approaches to measuring blood analytes," Clin. Chem., vol. 36, No. 8 Pt. 2, pp. 1562-1566 (1990).

Chira, I.S. et al, "Light scattering by blood components after supplying glucose," Biomed. Tech., vol. 35, No. 5, pp. 102-106 (1990).

Christison, G.B., et al, "Laser photoacoustic determination of physiological glucose concentrations in human whole blood," Med. Biol. Eng. Comput., vol. 31, No. 3, pp. 284-290 (1993).

Cote, G. L., et al, "Noninvasive optical polarimetric glucose sensing using a true phase measurement technique," IEEE Trans. Biomed. Eng., vol. 39, No. 7, pp. 752-756 (1992).

Drezek, R., et al, "Light scattering from cell: finite-difference time-domain simulations and goniometric measurements," Appl. Opt., vol. 38, No. 16, pp. 3651-3661 (1999).

Duck, F. A., Physical Properties of Tissue, (Academic London 1990).

Dyer, D. G., et al, "Accumulation of Maillard Reaction Products in Skin Collagen in Diabetes and Aging," J. Clin. Invest., vol. 91, pp. 2463-2469 (1993).

Fercher, A., et al, "In vivo optical coherence tomography," Amer. J. Opthalmol., vol. 116, No. 1, pp. 113-114 (1993).

Flock, S.T., et al, "Total attenuation coefficients and scattering phase functions of tissues and phantom materials at 633 nm," Med. Phys., vol. 14, No. 5, pp. 835-841 (1987).

Fogt, E.J., "Continuous ex vivo and in vivo monitoring with chemical sensors," Clin. Chem., vol. 36, No. 8 Pt. 2, pp. 1573-1580 (1990).

Frank, K.H., et al, "Measurements of angular distributions of Rayleigh and Mie scattering events in biological models," Phys. Med. Biol., vol. 34, No. 8, pp. 1901-1916 (1989).

Gabriely, I., et al, "Transcutaneous glucose measurement using near-infrared spectroscopy during hypoglycemia," Diabetes Care, vol. 22, No. 12, pp. 2026-2032 (1999).

Galanzha, E. I., et al, "Skin backreflectance and microvascular system functioning at the action of osmotic agents," J. Phys. D. Appl. Phys., vol. 36, pp. 1739-1746 (2003).

Gilbert, J.W., et al, "A cerebrospinal fluid glucose biosensor for diabetes mellitus," ASAIO J., vol. 38, No. 2, pp. 82-87 (1992).

Goetz Jr., M. J., et al, "Application of a multivariate technique to Raman spectra for quantification of body chemicals," IEEE Trans. Biomed. Eng., vol. 42, pp. 728-731 (1995).

Goodman, J. W., "Some fundamental properties of speckle," Journal of the Optical Society of America, vol. 66, No. 11, pp. 1145-1150 (Nov. 1976).

Gough, D.A., "The composition and optical rotary dispersion of bovine aqueous humor," Diabetes Care, vol. 5, No. 3, pp. 266-270 (May-Jun. 1982).

Gunby, P., "Laser-implant contact lens could be glucose monitor," JAMA, vol. 243, No. 4, pp. 317 (1980).

Guyton, A.C., Textbook of medical physiology, (W.B. Saunders Company 1992).

Huang, D., et al., "Optical Coherence Tomography," Science, vol. 254, pp. 1178-1181 (1991).

Huang, Y.L., et al, "On-line determination of glucose concentration throughout animal cell cultures based on chemiluminescent detection of hydrogen peroxide coupled with flow-injection analysis," J. Biotechnol., vol. 18, No. 1-2, pp. 161-172 (1991).

Kaiser, N., "Laser absorption spectroscopy with an ATR prism—noninvasive in vivo determination of glucose," Horm. Metab. Res. Suppl., vol. 8, pp. 30-33 (1979).

Kajiwara, K., et al, "Spectroscopic quantitative analysis of blood glucose by Fourier transform infrared spectroscopy with an attenuated total reflection prism," Med. Prog. Technol., vol. 18, No. 3, pp. 181-189 (1992).

Khalil, O. S., "Spectroscopic and clinical aspects of noninvasive glucose measurements," Clinical Chemistry, vol. 45, No. 2, pp. 165-177 (1999).

Kholodnykh, A. I., et al, "Precision of measurement of tissue optical properties with optical coherence tomography," Applied Optics, vol. 42, No. 16, pp. 3027-3037 (Jun. 1, 2003).

King, T. W., et al, "Multispectral polarimetric glucose detection using a single pockels cell," Optical Engineering, vol. 33 No. 8, pp. 2746-2753 (1994).

Kohl, M., et al, "The influence of glucose concentration upon the transport of light in tissue-simulating phantoms," Phys. Med. Biol., vol. 40, pp. 1267-1287 (1995).

Kohl, M., et al, "Influence of glucose concentration on light scattering in tissue-simulating phantoms," Optics Letters, vol. 19, No. 24, pp. 2170-2172 (Dec. 15, 1994).

Kruse-Jarres, J.D., "Physicochemical determinations of glucose in vivo," J. Clin. Chem. Clin. Biochem., vol. 26, No. 4, pp. 201-208 (1988).

Larin, K. V., et al, "Optoacoustic signal profiles for monitoring glucose concentration in turbid media," SPIE Proc., vol. 3726, pp. 576-583 (1988).

Larin, K. V., et al, "Specificity of noninvasive blood glucose sensing using optical coherence tomography technique: a pilot study," Physics in Medicine and Biology, vol. 48, pp. 1371-1390 (2003).

Larin, K. V., et al, "Phase-sensitive optical low-coherence reflectometry for the detection of analyte concentrations," Applied Optics, vol. 43, No. 17, pp. 3408-3414 (Jun. 10, 2004).

Lide, D.R., CRC Handbook of Chemistry and Physics, 79th ed. (CRC Press, Boca Raton, Florida, 1998).

MacKenzie, H. A., et al, "Advances in photoacoustic noninvasive glucose testing," Clin. Chem., vol. 45, No. 9, pp. 1587-1595 (1999).

Maier, J. S., et al, "Possible correlation between blood glucose concentration and the reduced scattering coefficient of tissues in the near infrared," Optics Letters, vol. 19, No. 24, pp. 2062-2064 (Dec. 15, 1994).

March, W., et al, "Optical monitor of glucose," Trans. Am. Soc. Artif. Intern. Organs, vol. 25, pp. 28-31 (1979).

March, W.F., et al, "Noninvasive glucose monitoring of the aqueous humor of the eye: Part II. Animal studies and the scleral lens," Diabetes Care, vol. 5, No. 3, pp. 259-265 (1982).

Mendelson, Y., et al, "Blood glucose measurement by multiple attenuated total reflection and infrared absorption spectroscopy," IEEE Trans. Biomed. Eng., vol. 37, No. 5, pp. 458-465 (1990).

Moreno-Bondi, M.C., et al, "Oxygen optrode for use in a fiber-optic glucose biosensor," Anal. Chem., vol. 62, No. 21, pp. 2377-2380 (1990).

Muller, A., "In vivo measurement of glucose concentration with lasers," Horm. Metab. Res. Suppl., vol. 8, pp. 33-35 (1979).

Narayanaswamy, R., "Current developments in optical biochemical sensors," Biosens. Bioelectron., vol. 6, No. 6, pp. 467-475 (1991).

Pan, S., et al, "Near-infrared spectroscopic measurement of physiological glucose levels in variable matrices of protein and triglycerides," Anal. Chem., vol. 68, pp. 1124-1135 (1996).

Peterson, J.I., et al, "A miniature fiberoptic pH sensor potentially suitable for glucose measurements," Diabetes Care, vol. 5, No. 3, pp. 272-274 (1982).

Quan, K. M., et al, "Glucose determination by a pulsed photoacoustic technique—an experimental study using a gelatin-based tissue phantom," Phys. Med. Biol., vol. 38, No. 12, pp. 1911-1922 (1993).

Rabinovitch, B., et al, "Noninvasive glucose monitoring of the aqueous humor of the eye: Part I. Measurement of very small optical rotations," Diabetes Care, vol. 5, No. 3, pp. 254-258 (1982).

Robinson, M. R., et al, "Noninvasive glucose monitoring in diabetic patients: A preliminary evaluation," Clin. Chem., vol. 38, No. 9, pp. 1618-1622 (1992).

Robinson, R.J., et al, "Glucose-sensitive membrane and infrared absorption spectroscopy for potential use as an implantable glucose sensor," ASAIO J., vol. 38, No. 3, pp. M458-M462 (1992).

Rusch, T. L. et al, "Signal Processing Methods for Pulse Oximetry," Comput. Biol. Med., vol. 26, No. 2, pp. 143-159 (1996).

Schmitt, J. M., et al, "Measurement of optical properties of biological tissues by low-coherence reflectometry," Applied Optics, vol. 32, No. 30, pp. 6032-6042 (1993).

Schmitt, J. M., et al, "Speckle in Optical Coherence Tomography," Journal of Biomedical Optics, vol. 4, No. 1, pp. 95-105 (Jan. 1999).

Sevick, E.M., et al, "Near-infrared optical imaging of tissue phantoms with measurement in the change of optical path lengths," Adv. Exp. Med. Biol., vol. 345, pp. 815-823 (1994).

Sodickson, L.A., et al, "Kromoscopic analysis: a possible alternative to spectroscopic analysis for noninvasive measurement of analysis in vivo," Clin. Chem., vol. 40, No. 9, pp. 1838-1844 (1994).

Star, W.M., et al, "Light dosimetry: status and prospects," J. Photochem. Photobiol., vol. 1, No. 2, pp. 149-167 (1987).

Stoddart, S., et al, "Pulse Oximetry: What it is and how to use it," Journal of Neonatal Nursing, pp. 10, 12-14 (Jul. 1997).

Takai, N., et al, "Studies of the development of optical fiber sensors for biochemical analysis," Artif. Organs, vol. 15, No. 2, pp. 86-89 (1991).

Tuchin, V. V., et al, "Light propagation in tissues with controlled optical properties," Journal of Biomed. Opt., vol. 2, No. 4, pp. 401-417 (1997).

Wang, L., et al, "Speckle reduction in laser projection systems by diffractive optical elements," Applied Optics, vol. 37, No. 10, pp. 1770-1775 (Apr. 1, 1998).

Weast, R. C., et al, CRC Handbook of Chemistry and Physics, 70th ed., (CRC Cleveland, Ohio 1989).

Welch, A.J., et al, "Practical models for light distribution in laser-irradiated tissue," Lasers Surg. Med., vol. 6, No. 6, pp. 488-493 (1987).

Wicksted, J. P., et al, "Monitoring of aqueous humor metabolites using Raman spectroscopy," SPIE Proc., vol. 2135, pp. 264-274 (1994).

Zeller, H., et al, "Blood glucose measurement by infrared spectroscopy," J. Artif. Organs, vol. 12, No. 2, pp. 129-135 (1989).

Kirill V. Larin, et al., "Noninvasive Blood Glucose Monitoring With Optical Coherence Tomography," Diabetes Care, vol. 25, No. 12, Dec. 2002, pp. 2263-2267.

Dirk J. Faber, et al., "Light absorption of (oxy-)hemoglobin assessed by spectroscopic optical coherence tomography," Optics Letters, vol. 28, No. 16, Aug. 15, 2003, pp. 1436-1438.

Joseph M. Schmitt, "Optical Coherence Tomography (OCT): A Review," IEEE Journal of Selected Topics in Quantum Electronics, vol. 5, No. 4, Jul./Aug. 1999, pp. 1205-1215.

Rinat O. Esenaliev, et al., "Noninvasive monitoring of glucose concentration with optical coherence tomography," Optics Letters, vol. 26, No. 13, Jul. 1, 2001, pp. 992-994.

Kirill V. Larin, et al., "Noninvasive Blood Glucose Monitoring With Optical Coherence Tomography", Emerging Treatment and Technology, vol. 25, No. 12, Dec. 2002, pp. 2263-2267.

Dirk J. Faber, et al., "Light absorption of 9oxy-)hemoglobin assessed by spectroscopic optical coherence tomography", Optics Letters, vol. 28, No. 16, Aug. 15, 2003, pp. 1436-1438.

Joseph M. Schmitt, "Optical Coherence Tomography (OCT): A Review", IEEE Journal of Selected Topics in Quantum Electronics, vol. 5, No. 4, Jul./Aug. 1999, pp. 1205-1215.

Rinat O. Esenaliev, et al., "Noninvasive monitoring of glucose concentration with optical coherence tomography", Optics Letters, vol. 26, No. 13, Jul. 1, 2001, pp. 992-994.

* cited by examiner

US 7,510,849 B2

OCT BASED METHOD FOR DIAGNOSIS AND THERAPY

CROSS REFERENCE TO RELATED APPLICATIONS

This application claims the benefit of U.S. Provisional Application Ser. No. 60/540,082 of the same title filed by the present inventors on Jan. 29, 2004.

FIELD OF THE INVENTION

The invention pertains to a method of using the signal derived from an Optical Coherence Tomography (OCT) sensor to monitor or diagnose the health of a subject or to apply therapeutic treatment. Specifically, the response of an OCT signal to oscillations in biological tissue over time in response to physiological perturbations can be used to gauge the health of the tissue, or the organ, system, or subject to which it belongs.

BACKGROUND OF THE INVENTION

In medicine, the health of a subject is frequently monitored via the periodicity of certain biological processes. For example an electrocardiogram measures the periodic impulses of the heart in a wide variety of diagnostic tests. From this periodic signal the health of the heart or other organs can be monitored. Another way to assess a subject's health is to introduce a perturbation in the subject's response and measure the response to that change. An example is the oral glucose tolerance test, where the insulin response of a subject is tested by challenging the subject's body with a high glucose load. The rise and fall of glucose levels in the blood guides the diagnosis of diabetes.

Optical Coherence Tomography (OCT) is an optical backscatter technique, analogous to a sonogram, that is used to create high resolution images of tissues (several microns) at relatively shallow depths (a few mm). ("*Optical Coherence Tomography (OCT): A Review*", J. M. Schmitt, IEEE Journal of Selected Topics in Quantum Electronics, July/August 1999, p. 1205). Recently, this technique has been applied to monitor blood glucose. ("*Noninvasive Blood Glucose Monitoring With Optical Coherence Tomography, A pilot Study in Human Subjects*", K. Larin, et al., Diabetes Care, vol. 25, no. 12, December 2002, See also: R. O. Esenaliev et al., "*Noninvasive Blood Glucose Monitoring With Optical Coherence Tomography*", Diabetes Care, Volume 25, Number 12, December 2002) and blood oxygenation (oximetry). ("*Light absorption of (oxy-)hemoglobin assessed by spectroscopic optical coherence tomography*", D. J. Faber et al., Optics Letters, 2003, pgs. 1436-1438). An OCT method for brain oximetry is disclosed in U.S. Provisional Patent Application Ser. No. 60/485,761, "*Method and Apparatus for Brain Oximetry*", filed by M. J. Schurman on Jul. 9, 2003. The 60/485,761 application is attached hereto.

In these sensor applications the change in the intensity of the reflected light from the tissue can be related to changes in the tissue being probed. Such changes can be due, for example, to variations in osmolyte concentrations, cell volume, or fluid volume surrounding the cells. The great strength of OCT sensors is that the small light/tissue interaction volume that they probe provides information on tissue changes at a highly localized level. Also, OCT measurements can be made continuously, thus providing a monitoring capability that was previously unavailable. One example of continuous monitoring, according to the prior art, is illustrated by FIGS. 1 and 2, which show, respectively, an OCT sensor signal from the skin and a blood glucose measurement as a function of time using standard assay techniques. In this test, a healthy subject was given a drink of glucose to induce an insulin response that serves to reduce the glucose levels in the subject. These tests are used routinely by doctors in the diagnosis of diabetes, however it is the macro-response of the human body over a period of three hours that doctors use to guide diagnosis.

It would be advantageous to have a method and apparatus to observe the response of the human body to this and other types of stimulus over shorter time scales.

SUMMARY OF THE INVENTION

This invention relates to a method of diagnosing or treating a biological subject, such as a person or animal, comprising the steps of subjecting at least a microsample of the subject's tissue to a physiological perturbation and measuring the response of the microsample to the perturbation using optical coherence tomography (OCT). In an exemplary embodiment, the concentration of glucose in the microsample is perturbed, as by providing the subject with a high glucose drink, and subsequently monitoring at a high sample rate in a microsample by OCT. Pathology, such as diabetes, can be diagnosed by deviation of the concentration vs. time response over several cells (micro-oscillation) from the micro-oscillation in the cells of a healthy subject. Other applications include diagnosing or treating de-hydration and diseases that cause changes in the osmolyte concentrations and thus the osmotic pressure in the cells in tissue.

DRAWINGS

The advantages, nature and various additional features of the invention will appear more fully upon consideration of the illustrative embodiments now to be described in detail in connection with the accompanying drawings. In the drawings.

Figure 1:
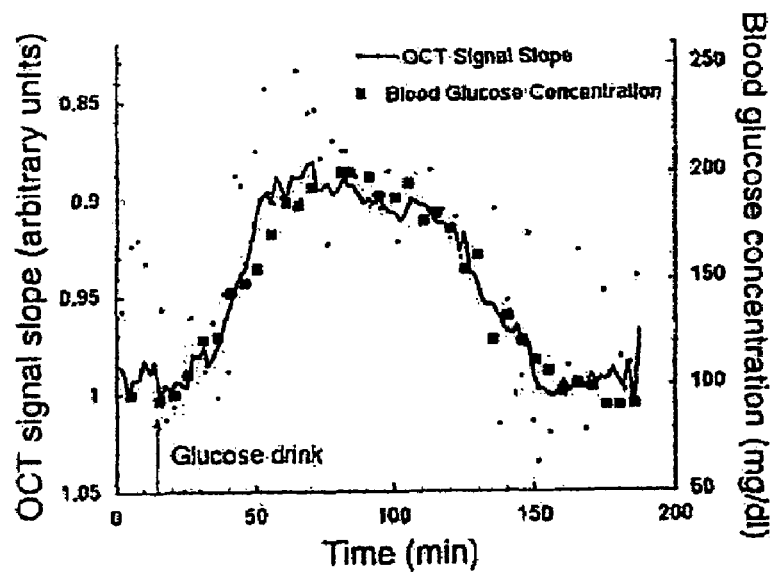
FIG. 1 shows OCT vs. blood glucose measurements taken over a long time scale during an oral glucose tolerance test (Larin, et al.)
Figure 2:
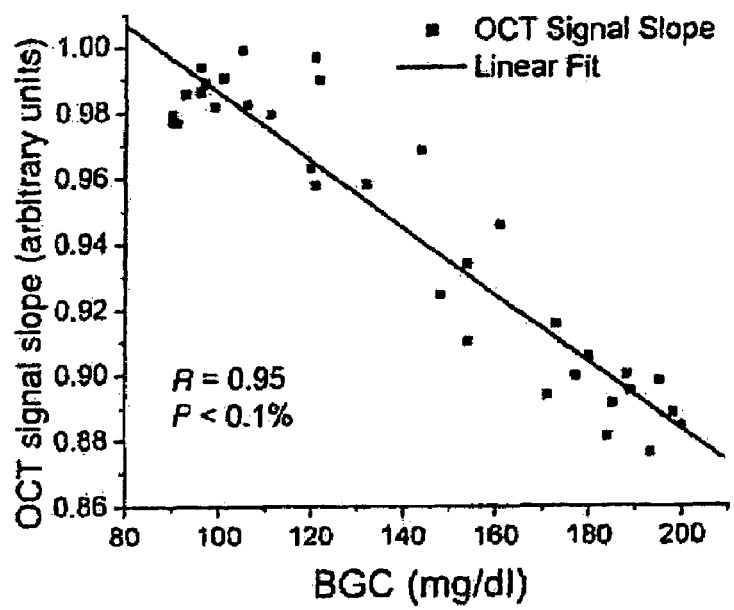
FIG. 2 shows the slope of OCT signals versus blood glucose concentration for the test of FIG. 1 (Larin, et al.)

It is to be understood that these drawings are for illustrating the concepts of the invention and, except for some graphs, are not to scale.

DETAILED DESCRIPTION

High frequency measurements of micro-oscillations can show the local response, in both frequency and amplitude, of a tissue or organ (such as skin cells) to a macroscopic perturbation (such as an oral glucose tolerance test). The oscillatory behavior in time of the scatter coefficient of tissue, as measured via an OCT sensor, can be used to determine the health of tissue, organs, and/or human and animal subjects. The oscillatory signal may also be used to guide treatment, as for example, to supply insulin to the body in a way that more closely mimics actual insulin production in the pancreas so as to minimize undesirable side effects of therapeutic insulin administration.

Micro-oscillations of the scatter coefficient can be due to changes in osmolyte concentrations (such as glucose), tissue perfusion, cellular volume change, etc. Such oscillations can be due to natural biorhythms in the tissues, organ, or subject with deviations from a "normal" signal used to gauge health. In the case of glucose, levels within the tissue itself are being observed by the inventive method. These observations are short time scale representations of the biological processes occurring within the tissue where the glucose is being taken up and the insulin is interacting with the glucose in the cells or interstitial fluid. This is believed to be caused by the osmolality (osmatic pressure) of the cells in the tissue.

Micro-oscillations can be induced intentionally via external perturbation (such as an oral glucose tolerance test) or may occur naturally and the response of the tissue can then be monitored in order to determine the health of the tissue, organ, or subject. Such perturbations can be on the macroscopic scale (i.e. subject drinks heavy glucose load such as in the oral glucose tolerance test) or on the microscopic scale (i.e. local heating or cooling of the tissue). In all the above cases, the localized information provided by the OCT sensor is used to monitor the local tissue scatter coefficient changes. Drinks, intravenous ("IV"), or other solutions or chemicals introduced into the body, that can cause a change in the osmolyte levels of tissue cells, can be useful as potential agents to perturb the tissue biological systems to induce micro-oscillations.

Other potential causes of this type of perturbation include, for example the post trauma response of the body, post surgery, psychological stress such as in combat, physical stress such as in running a marathon, pre-gestational diabetes, fatigue, diet, the aging process, infection, birth defects, and other conditions that cause a response from the pancreas. These perturbations can lead to characteristic signatures in the short time scale micro-oscillations which may be useful in diagnosis of the respective condition.

It is expected that oscillations detected by the inventive method can indicate body electrolyte levels as for example, related to various stages and states of physical activity and exercise. The diagnostic is likely a sensitive indicator of dehydration and thus also an indicator of conditions that can cause dehydration.

The OCT sensor can be applied to monitoring the blood glucose levels in humans and animals to observe, measure and record micro-oscillations of the signal over short time periods on the order of 10 minutes or less. Corresponding useful sample rates are less then 5 minutes, and preferably 2 minutes or less. By comparison, the standard blood assay is typically done at 30 minute sampling intervals. Micro-oscillations, are oscillatory changes in time of the scattering coefficient of tissue on the physical scale of tens of microns or over small groups of cells. Micro refers to the very small physical area of the tissue or surface of the organ of the subject being measured or to a larger surface area with a shallow depth on the order of tens of microns (as opposed to the short time scale of the OCT response). Micro-oscillations can be induced by some perturbation of the biological system. It is expected that there will be pronounced change in this signal in response to a perturbation in an unhealthy subject, especially over short time scales heretofore uninvestigated. Changes are expected in the amplitude, frequency, and wave shape of the micro-oscillations in unhealthy subjects.

Figure 3:
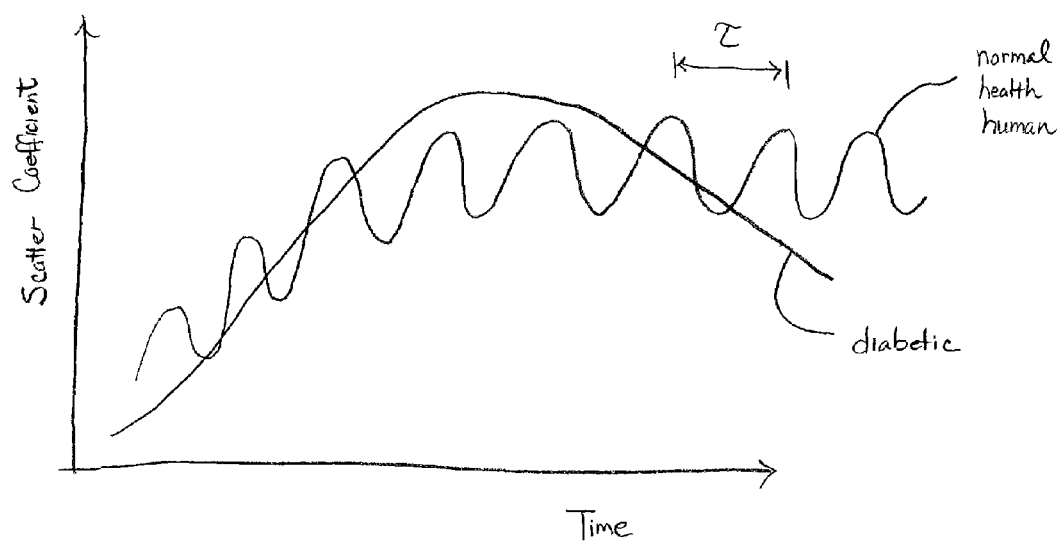
FIG. 3 is an exemplary sketch of the predicted OCT micro-oscillations for a diabetic versus a healthy subject.

FIG. 3 is an exemplary sketch according to the inventive technique showing the predicted OCT response of a diabetic versus a healthy human's skin scattering coefficient to rising glucose levels. The healthy human shows a rise in scatter coefficient accompanied by a micro-oscillation whose period (shown as $\tau$) is constant throughout the glucose rise. For the diabetic, no oscillation is apparent. A diabetic may have an oscillation as well but that period will be vastly different, or even non-constant in response to changing glucose levels.

The oscillations that are observed from tissue can be used to characterize the health of the tissue being observed and/or the health of an organ or system. This may be accomplished in one of three ways. First, the frequency of the oscillation may relate to the efficiency or health of the subject under observation. Second, the amplitude of the oscillations may also relate to the subjects health. Third, the impulse response of the oscillations to a rapid external perturbation may relate to a tissue or organ's ability to recover from an external perturbation and reveal more on the health of the system.

Previous studies have observed relatively slow oscillations on far longer time scales. In the case of glucose sensitivity, oscillations have been observed to have a characteristic frequency and amplitude for a given subject. A typical long time scale oscillation curve of a healthy subject is shown in FIG. 1.

Figure 4:
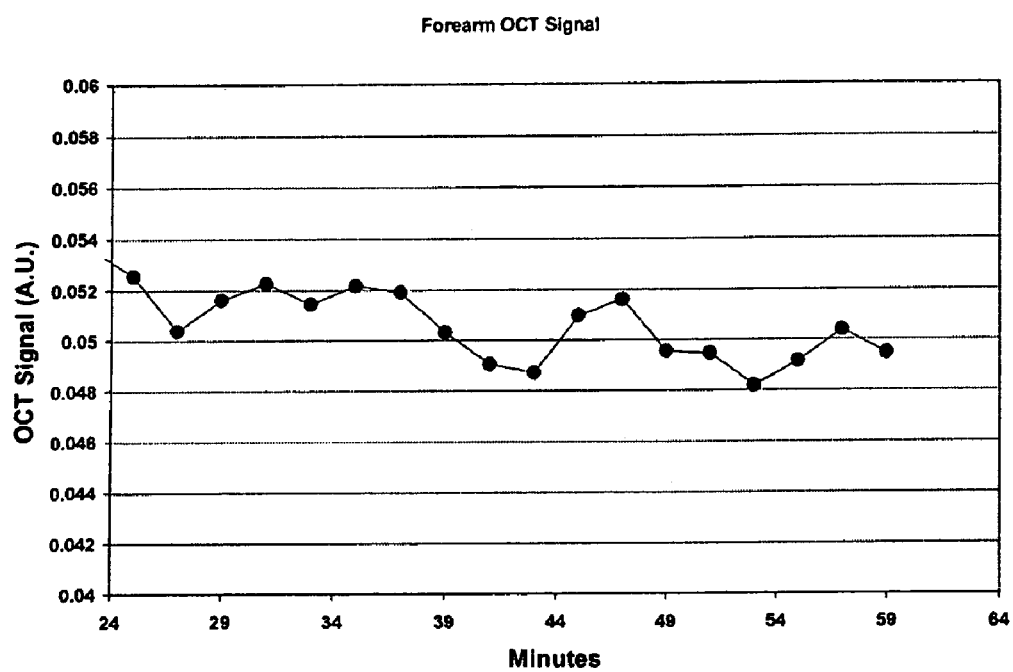
FIG. 4 shows an OCT signal taken from the skin of the forearm of a healthy human subject. Data taken at 2 minute intervals.

FIG. 4 shows the signal from a healthy human subject's forearm, in the absence of a large perturbation in the blood glucose level (i.e. not oral glucose tolerance test). The period of the micro-oscillation is roughly 10 minutes. Although the sources of these oscillations are not currently well understood, their magnitude can also be observed to change as a function of a macro-perturbation.

Figure 5:
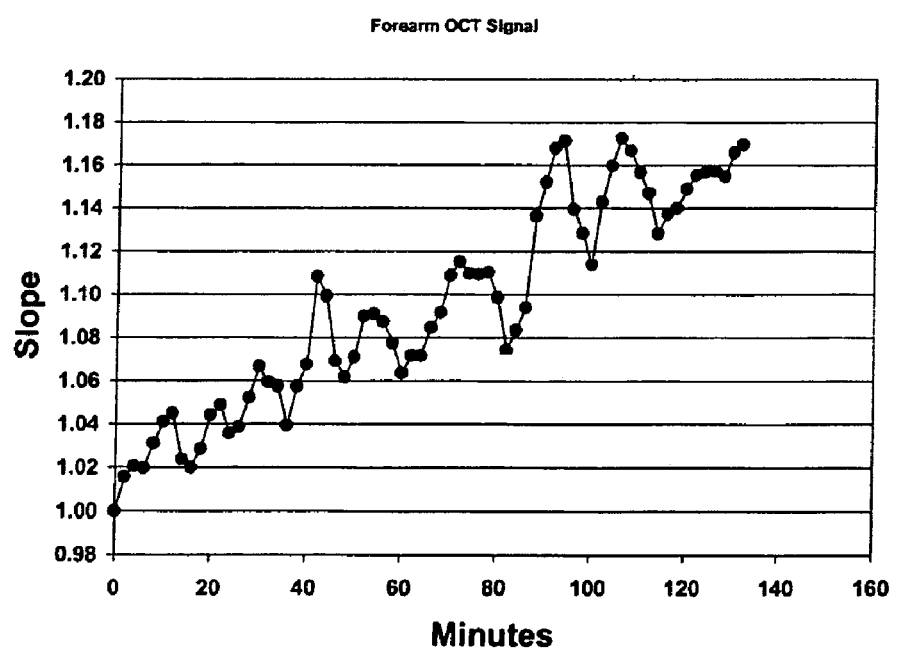
FIG. 5 shows an OCT signal taken from the skin of the forearm of a healthy human subject that has drunk a 75 mg load of fructose after an overnight fast.

In FIG. 5, the OCT signal as a function of time from another healthy human subject's forearm can be observed to be rising, due to a ~76 mg fructose load given after an overnight fast. Although the overall rise in the signal is expected (glucose levels in the blood can be expected to rise in such a case), what is not expected nor previously observed is the 10 minute micro-oscillations in the data. Further, it appears that as the overall glucose level rises (as determined via a rise in the normalized OCT signal) the amplitude of the micro-oscillations can also be seen to increase. It is this signature micro-oscillation that can be a fingerprint for the health of a tissue, organ, system, or subject. In the case of glucose, the insulin response of a subject may be related to the magnitude and period of the micro-oscillations, with more random frequency of the swings, or greater amplitude of the oscillations. These can then be related back to the insulin response of the person and can be used to diagnose diabetes.

Another application might be to modulate insulin dosing in a diabetic so that the signal received by the OCT scanner mimics the response seen in a healthy human. This more cell friendly way of applying therapeutic insulin treatment can reduce complications and side effects of the disease and lead to a greater life expectancy of the patient. Specifically, in the case of continuous insulin administration as for example in an insulin pump, the micro-oscillations of glucose over time in the interstitial fluid and as shown by the OCT signal can be applied to the pump control to more faithfully reproduce the body's own insulin production.

In the case of OCT of the skin, the dominant effect on the signal is due to glucose changes. However, by modifying the wavelength of the OCT sensor, the tissue type probed, or modifying the OCT system for polarization sensitivity (as examples), different physiological changes can be monitored and their micro-oscillatory response over time may prove equally as useful in monitoring and/or diagnosing health.

It is understood that the above-described embodiments are illustrative of only a few of the many possible specific embodiments, which can represent applications of the invention. Numerous and varied other arrangements can be made by those skilled in the art without departing from the spirit and scope of the invention. The examples represent the best current understanding of the use of short time scale OCT measurements of micro-oscillations for the diagnosis and control of physiological processes in humans and animals.

What is claimed is:

1. A method of characterizing a patient's blood glucose concentrations based on optical coherence tomography, the method comprising:
    employing optical coherence tomography to measure light reflected from a patient's skin tissue at a plurality of depths;
    determining a tissue scattering coefficient for a tissue region based on differences in light reflected at different depths;
    detecting micro-oscillations in the tissue scattering coefficient over a time interval; and
    relating the micro-oscillations to the patient's blood glucose concentrations.

2. The method of claim 1, wherein the step of employing optical coherence tomography to measure reflected light further comprises obtaining a plurality of reflected light intensity measurements at varying tissue depths, each measurement obtained by interfering a tissue-reflected light beam with a reference-reflected light beam, the path length of the reference-reflected light beam determining a tissue depth for each measurement.

3. The method of claim 1, wherein the step of determining a tissue scattering coefficient for a tissue region further comprises selecting a function that describes a relationship between reflected light measurements and their corresponding depths and applying the function to determine the scattering coefficient.

4. The method of claim 3, wherein the function is a slope function.

5. The method of claim 1, wherein the method further comprises detecting micro-oscillations having a period less than about 20 minutes.

6. The method of claim 1, wherein the step of relating the micro-oscillations further comprises relating a period of the micro-oscillations to a patient's insulin response to blood glucose concentrations.

7. The method of claim 1, wherein the step of relating the micro-oscillations further comprises relating an amplitude of the micro-oscillations to a patient's insulin response to blood glucose concentrations.

8. The method of claim 1, wherein the patient has diabetes.

9. The method of claim 1, wherein the step of relating the micro-oscillations further comprises relating the micro-oscillations with an insulin response in the patient.

10. The method of claim 1, wherein the method further comprises providing a glucose sample to the patient.

11. The method of claim 10, wherein the method further comprises relating a condition of the tissue with an impulse response due to the glucose sample.

12. The method of claim 1, further comprising:
    modulating insulin dosing in the patient such that micro-oscillations of the tissue scatter coefficient in the patient approach a normal micro-oscillation response to glucose dosing in a healthy patient.

13. The method of claim 1, wherein the step of relating the micro-oscillations further comprises characterizing health of an organ or system of the patient based upon the detected micro-oscillations in the tissue scattering coefficient over the time interval.

* * * * *